United States Patent
Joung et al.

(10) Patent No.: US 11,717,509 B2
(45) Date of Patent: *Aug. 8, 2023

(54) BLEND CONTAINING CARBAMATE COMPOUND FOR PREVENTION, MITIGATION, OR TREATMENT OF SCHIZOPHRENIA

(71) Applicant: SK BIOPHARMACEUTICALS CO., LTD., Gyeonggi-do (KR)

(72) Inventors: Chan Mi Joung, Gyeonggi-do (KR); Sun Gwan Hwang, Gyeonggi-do (KR); Ji Won Lee, Gyeonggi-do (KR); Young Koo Jang, Gyeonggi-do (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 72 days.

This patent is subject to a terminal disclaimer.

(21) Appl. No.: 17/397,177

(22) Filed: Aug. 9, 2021

(65) Prior Publication Data

US 2021/0361622 A1  Nov. 25, 2021

Related U.S. Application Data

(63) Continuation of application No. 16/763,604, filed as application No. PCT/KR2018/013769 on Nov. 13, 2018, now Pat. No. 11,116,751.

(30) Foreign Application Priority Data

Nov. 14, 2017  (KR) .................. 10-2017-0151253

(51) Int. Cl.
*A61K 31/41* (2006.01)
*A61K 31/496* (2006.01)

(52) U.S. Cl.
CPC ............ *A61K 31/41* (2013.01); *A61K 31/496* (2013.01)

(58) Field of Classification Search
CPC .................................................. A61K 31/41
See application file for complete search history.

(56) References Cited

U.S. PATENT DOCUMENTS

| 2012/0004211 A1 | 1/2012 | Jagerovic et al. |
| 2017/0029382 A1 | 2/2017 | Bosmans et al. |

FOREIGN PATENT DOCUMENTS

| KR | 10-1286499 B1 | 7/2013 |
| WO | WO-2006-048771 A1 | 5/2006 |
| WO | WO-2006-112685 A1 | 10/2006 |
| WO | WO-2010-150946 A1 | 12/2010 |
| WO | WO-2011-046380 A2 | 4/2011 |
| WO | WO-2013-131018 A1 | 9/2013 |
| WO | WO-2017-066590 A1 | 4/2017 |
| WO | WO-2017/075222 A1 | 5/2017 |

OTHER PUBLICATIONS

International Search Report from corresponding PCT Application No. PCT/KR2018/013769, dated Feb. 19, 2019.
Bialer, M., et al., "Progress Report on New Antiepileptic Drugs: A Summary of the Twelfth Eilat Conference (Eilat XII)", Epilepsy Research, vol. 111, 2015, pp. 85-141.
Imbrici, P., et al.; "Major Channels Involved in Neuropsychiatric Disorders and Therapeutic Perspectives", Frontiers in Genetics, May 2013, vol. 4, article 76, pp. 1-19.
Neill, J. C., et al.; "Effects of cariprazine, a novel antipsychotic, on cognitive deficit and negative symptoms in a rodent model of schizophrenia symptomatology", European Neuropsychopharmacology (2016) 26, 3-14.
Rung, J. P., et al.; "(+)-MK-801 induced social withdrawal in rats; a model for negative symptoms of schizophrenia", Progress in Neuro-Psychopharmacology & Biological Psychiatry 29 (2005) 827-832.
Deiana, S., et al.; "MK-801-induced deficits in social recognition in rats: reversal by aripiprazole, but not olanzapine, risperidone, or cannabidiol", Behavioural Pharmacology 2015, 26:748-765.
L. Faravelli et al., European Neuropsychopharmacology, 2016, vol. 26, Supplement 2, p. S588.
S.S. Chung et al., Epilepsy Curr., 2014, vol. 14, Suppl, pp. 1,438.
G. Zaccara et al., Current Pharmaceutical Design, 2017, vol. 23, pp. 5593-5605.
Extended European Search Report from corresponding European Patent Application No. 18878582.8, dated Oct. 27, 2021.
"Annual Updated 2003: Drugs for Psychiatric Disorders and Substance Abuse", Drugs of the Future, Prous Science, ES, 2003, vol. 28, No. 11, pp. 1103-1144.
Mealy, N.E., et al.; "Update 2006—Treatment of Psychiatric Disorders—Treatment of Psychiatric Disorders by Condition", Drugs of the Future, Prous Science, ES, 2006, vol. 31, No. 3, pp. 259-284.

*Primary Examiner* — Kamal A Saeed
(74) *Attorney, Agent, or Firm* — Harness, Dickey & Pierce, P.L.C.

(57) ABSTRACT

The present invention relates to a blend for prevention, mitigation, or treatment of schizophrenia, the blend containing a carbamate compound of chemical formula 1, or a pharmaceutically acceptable salt, solvate, or hydrate thereof and, more specifically, to a blend and a pharmaceutical composition each containing a carbamate compound of chemical formula 1 and aripiprazole, and to a use thereof for treating schizophrenia.

17 Claims, 1 Drawing Sheet

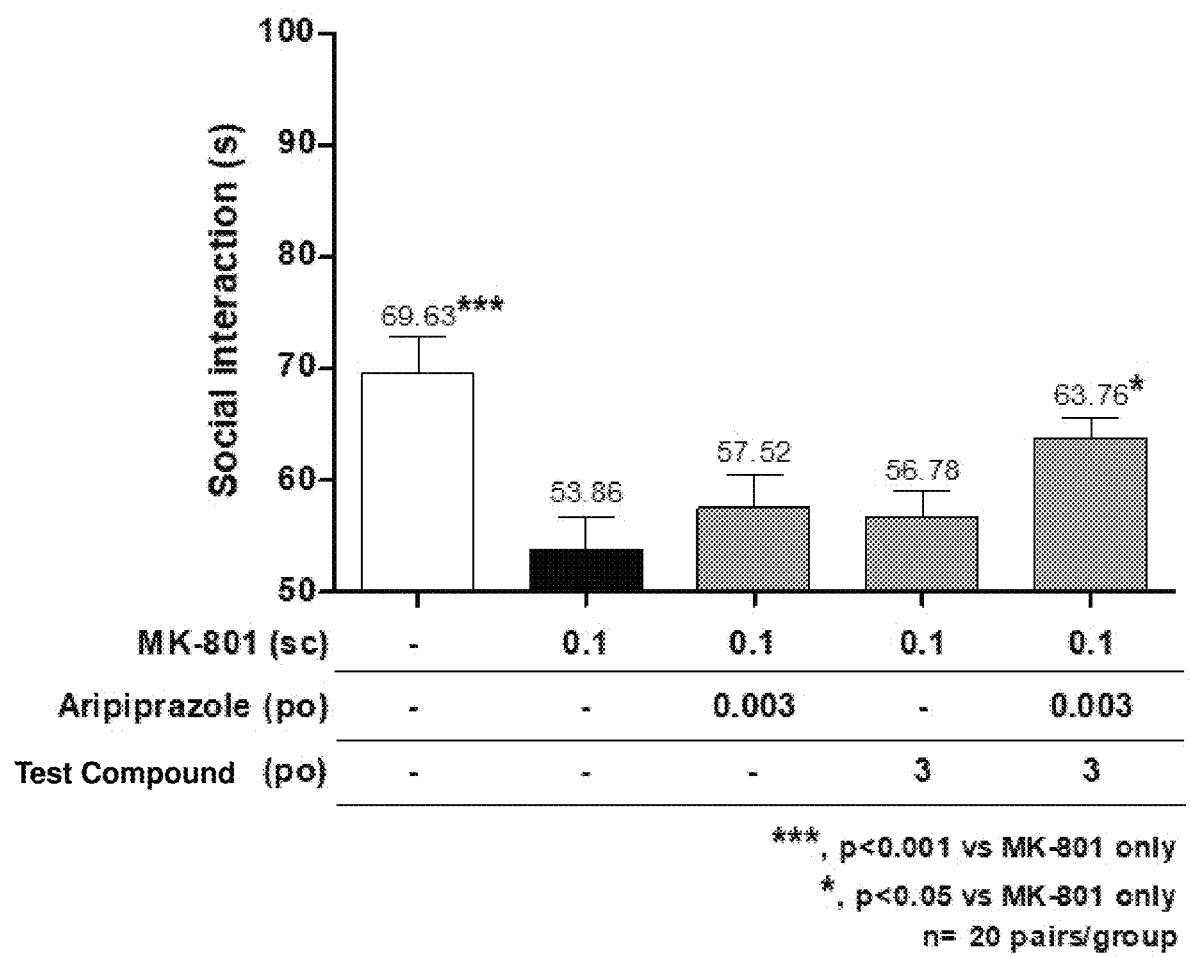

BLEND CONTAINING CARBAMATE COMPOUND FOR PREVENTION, MITIGATION, OR TREATMENT OF SCHIZOPHRENIA

CROSS-REFERENCE TO RELATED APPLICATIONS

This application is a continuation application of U.S. application Ser. No. 16/763,604, filed on May 13, 2020, which is a national phase application of PCT Application No. PCT/KR2018/013769, filed on Nov. 13, 2018, which claims priority to Korean Patent Application No. 10-2017-0151253, filed on Nov. 14, 2017. The entire disclosure of the applications identified in this paragraph is incorporated herein by reference.

FIELD

The present invention relates to a combination comprising a carbamate compound of the following Formula 1, or a pharmaceutically acceptable salt, solvate or hydrate thereof for preventing, alleviating or treating schizophrenia, more specifically to a combination comprising the carbamate compounds of Formula 1 and aripiprazole:

[Formula 1]

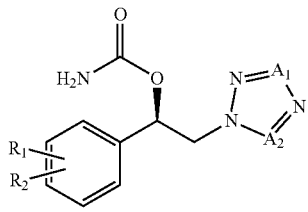

wherein,
$R_1$, $R_2$, $A_1$ and $A_2$ are as defined herein.

BACKGROUND

Schizophrenia, a representative psychiatric disorder, is a syndrome of various psychotic symptoms in which the main pathology is a thought disorder and complex symptoms appear in various areas such as speech, behavior, emotion and cognition that are associated with or derived from such thought disorder. It is a series of symptoms that have long been called madness in human history.

In general, the prevalence of schizophrenia is approximately 1% of the world's population and has been observed to be constant regardless of population characteristics, and regional and cultural differences, such as Western and Eastern, and developed countries and developing countries. Although the cause of schizophrenia is not clear, its likelihood of development is said to increase due to genetic predisposition or environmental factors such as problems during pregnancy, parenting environment and stress.

Symptoms of schizophrenia can be classified into a positive symptom, a negative symptom, a cognitive symptom and a residual symptom. Positive symptoms refer to abnormal and bizarre symptoms that appear externally, psychotic symptoms that cannot be found in healthy people, including abnormalities in sense such as auditory hallucinations or visual hallucinations; abnormalities in thoughts such as unrealistic and bizarre delusions; and disorders in the thinking process in which an abnormality occurs in the flow of thought. Negative symptoms refer to a phenomenon in which a normal emotional reaction or behavior decreases to become a dull state and which show poverty of the content of thought, decrease in motivation, social withdrawal, etc. Negative symptoms generally do not respond better to medication than positive symptoms. Cognitive symptoms refer to symptoms showing difficulty in maintaining concentration and a decrease in the ability to learn new information or organize one's thoughts. These symptoms make patients unable to do what they used to do well in the past, and significantly reduce memory and problem-solving ability, thereby degrading the patients' social and occupational functions, causing the patients to fail to return to society and to become unemployed and to experience frustration. Cognitive symptoms refer to symptoms showing difficulty in maintaining concentration and a decrease in the ability to learn new information or organize one's thoughts. Patients are not able to do what they used to do well in the past, and show a significant reduction in memory and problem-solving ability. Cognitive symptoms are less noticeable, but decrease the social and occupational functions of schizophrenia patients, causing them to fail to return to society and to experience frustration.

Schizophrenia can be presented in various forms depending on the symptoms and signs as described above. Schizophrenia includes not only paranoid schizophrenia, disorganized schizophrenia, catatonic schizophrenia and undifferentiated schizophrenia, but also post-schizophrenic depression, residual schizophrenia, simple schizophrenia and unspecified schizophrenia. In addition thereto, schizophreniform disorder, schizoaffective disorder, delusional disorder, brief psychotic disorder, shared psychotic disorder, psychotic disorder due to another medical condition, substance/medication-induced psychotic disorder, or psychotic disorder of unknown cause are included in schizophrenia in a broad sense.

Typical antipsychotic drugs such as haloperidol and chlorpromazine, and atypical antipsychotic drugs such as aripiprazole, risperidone and clozapine have been developed, and these drugs are known to be effective especially for the positive symptoms of schizophrenia. When patients start medication, psychomotor agitation, hallucinations, etc. of the acute phase generally improve within a few days, and delusions also improve within a few weeks. It is known that in most patients, a significant portion of the acute phase symptoms improves when the appropriate medication is maintained at the appropriate dose for 6-8 weeks. However, when patients first take antipsychotic drugs, many of them experience drowsiness and dizziness, and they often experience blurred vision, palpitations, menstrual changes and skin rashes.

Conventional antipsychotic drugs alleviate or relieve the symptoms of patients to improve the quality of life, but this does not induce complete healing and their use is limited due to side effects. Hence, these drugs have limited therapeutic value in the management of schizophrenia, and there is a need to develop new drugs with improved drug efficacy and side effects. In particular, no drug is presently satisfactory to treat the negative or cognitive symptoms of schizophrenia, and thus development of such a drug is necessary.

SUMMARY

Problem to be Solved

The present invention is intended to provide a combination and a pharmaceutical composition that exhibits an improved effect in the prevention, alleviation or treatment of schizophrenia without increasing side effects.

Technical Solution to the Problem

The present inventors have thought that combining the conventional (existing) antipsychotic agents such as aripiprazole with drugs having different mechanisms of action could maintain or elevate their efficacy while reducing side effects by decreasing the dose required for the efficacy of the conventional antipsychotic agents, and thus have conducted a thorough study.

As a result, the present inventors have selected a carbamate compound of the following Formula 1, or a pharmaceutically acceptable salt, solvate or hydrate thereof, as a drug having a mechanism of action different from that of the conventional antipsychotic agents:

[Formula 1]

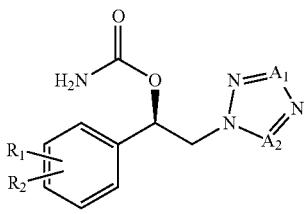

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

In addition, as the conventional antipsychotic agent, the present inventors have selected an atypical antipsychotic agent from the group consisting of aripiprazole, asenapine, clozapine, iloperidone, olanzapine, lurasidone, paliperidone, quetiapine, risperidone and ziprasidone. In one embodiment of the present invention, the atypical antipsychotic agent is aripiprazole.

Thus, as one specific aspect, the present invention provides a combination for the prevention, alleviation or treatment of schizophrenia, comprising (a) a carbamate compound of Formula 1, or a pharmaceutically acceptable salt, solvate or hydrate thereof; and (b) aripiprazole, or a pharmaceutically acceptable salt, solvate or hydrate thereof.

In addition, the present invention provides a pharmaceutical composition for the prevention, alleviation or treatment of schizophrenia, comprising as active ingredients (a) a carbamate compound of Formula 1, or a pharmaceutically acceptable salt, solvate or hydrate thereof; and (b) aripiprazole, or a pharmaceutically acceptable salt, solvate or hydrate thereof; and further one or more of a pharmaceutically acceptable carrier.

In addition, the present invention provides a kit for the prevention, alleviation or treatment of schizophrenia, comprising (a) a first composition comprising a carbamate compound of Formula 1, or a pharmaceutically acceptable salt, solvate or hydrate thereof; and (b) a second composition comprising aripiprazole, or a pharmaceutically acceptable salt, solvate or hydrate thereof, in a container.

Effect of the Invention

The combination and pharmaceutical composition of the present invention provide an improved effect of prevention, alleviation or treatment of schizophrenia without increasing side effects. In one embodiment, the combination and pharmaceutical composition of the present invention exhibit a synergistic effect in the prevention, alleviation or treatment of schizophrenia. In particular, the combination and pharmaceutical compositions of the present invention are effective in treating negative symptoms of schizophrenia or ameliorating cognitive impairment.

In addition, by selecting the carbamate compounds of Formula 1 as a drug having a mechanism of action different from that of the existing antipsychotic agents, and combining said carbamate compounds with the existing atypical antipsychotic drug, aripiprazole, the combination and pharmaceutical composition of the present invention can reduce the side effects of the existing antipsychotic drugs while maintaining or elevating the drug efficacy even though the dose required for the drug efficacy is reduced.

BRIEF DESCRIPTION OF THE DRAWINGS

FIG. 1 shows the results of a test compound and aripiprazole of the social interaction animal behavior test related to negative symptoms of schizophrenia in an animal model in which schizophrenia-like symptoms were induced by treatment with dizocilpine (MK-801). Description of each symbol in FIG. 1 is as follows:
Social interaction=the total amount of time spent in active social interaction
s=seconds
sc=mg/kg, subcutaneously
po=mg/kg, per os
-=Not treated

DETAILED DESCRIPTION

Hereinafter, the present invention will be described in detail.

The present invention provides a combination for the prevention, alleviation or treatment of schizophrenia, comprising (a) a carbamate compound of the following Formula 1, or a pharmaceutically acceptable salt, solvate or hydrate thereof; and (b) aripiprazole, or a pharmaceutically acceptable salt, solvate or hydrate thereof:

[Formula 1]

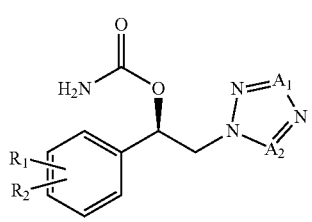

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

In addition, the present invention provides a pharmaceutical composition for the prevention, alleviation or treatment of schizophrenia, comprising as active ingredients (a) a carbamate compound of Formula 1, or a pharmaceutically acceptable salt, solvate or hydrate thereof; and (b) aripiprazole, or a pharmaceutically acceptable salt, solvate or hydrate thereof; and further one or more of a pharmaceutically acceptable carrier.

In addition, the present invention provides a kit for the prevention, alleviation or treatment of schizophrenia, comprising (a) a first composition comprising a carbamate compound of Formula 1, or a pharmaceutically acceptable salt, solvate or hydrate thereof; and (b) a second composition comprising aripiprazole, or a pharmaceutically acceptable salt, solvate or hydrate thereof, in a container.

In addition, the present invention provides a method for preventing, alleviating or treating schizophrenia, comprising administering to a subject in need of such treatment a therapeutically effective amount of (a) a carbamate compound of Formula 1, or a pharmaceutically acceptable salt, solvate or hydrate thereof; and of (b) aripiprazole, or a pharmaceutically acceptable salt, solvate or hydrate thereof.

In addition, the present invention provides the use of a combination comprising (a) a carbamate compound of Formula 1, or a pharmaceutically acceptable salt, solvate or hydrate thereof; and (b) aripiprazole, or a pharmaceutically acceptable salt, solvate or hydrate thereof, for the prevention, alleviation or treatment of schizophrenia.

According to one embodiment of the present invention, in the above combination the components (a) and (b) may be administered simultaneously, separately or sequentially.

According to one embodiment of the present invention, in the above kit (a) the first composition and (b) the second composition may be administered simultaneously, separately or sequentially.

According to one embodiment of the present invention, in the above method of prevention, alleviation or treatment, the components (a) and (b) may be administered to the subject simultaneously, separately or sequentially.

According to one embodiment of the present invention, in the above use the components (a) and (b) may be administered simultaneously, separately or sequentially.

In one embodiment of the present invention, in the above Formula 1, $R_1$ and $R_2$ are each independently selected from the group consisting of hydrogen, halogen and $C_1$-$C_8$ alkyl.

In one embodiment of the present invention, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl-ethyl ester of the following Formula 2:

[Formula 2]

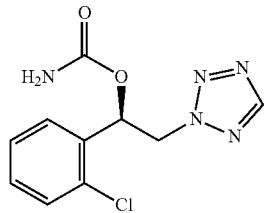

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

Aripiprazole is a product marketed under the trade name Ability®. The chemical name is 7-{4-[4-(2,3-dichlorophenyl)piperazin-1-yl]butoxy}-3,4-dihydroquinolin-2(1H)-one, and the structure is as follows:

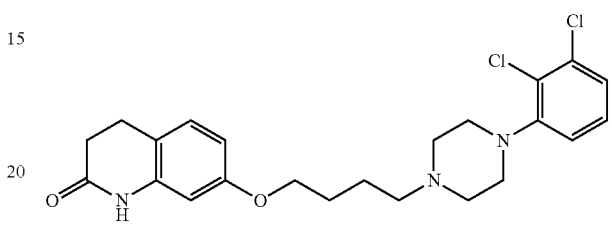

In one embodiment of the present invention, in addition to aripiprazole, an atypical antipsychotic agent selected from the group consisting of asenapine, clozapine, iloperidone, olanzapine, lurasidone, paliperidone, quetiapine, risperidone and ziprasidone may also be preferably used.

In the present invention, as the compounds of the above Formula 1 or 2 and aripiprazole, their free form, or a pharmaceutically acceptable salt, solvate or hydrate thereof, may be used.

According to one embodiment of the present invention, as the compounds of the above Formula 1 or 2 and aripiprazole, their free form may be used.

For instance, examples of the pharmaceutically acceptable salts of the compounds of the above Formula 1 or 2, or the pharmaceutically acceptable salts of aripiprazole, include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemi-succinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

In the combination or pharmaceutical composition according to one embodiment of the present invention, a therapeutically effective amount or dose of the compounds of Formula 1 may include 12.5 to 500 mg, 12.5 to 400 mg, 25 to 400 mg, 25 to 300 mg, 25 to 200 mg, 50 to 400 mg, 50 to 300 mg, 50 to 200 mg, or 100 to 200 mg, based on the free form and once-daily administration to humans.

In the combination or pharmaceutical composition according to one embodiment of the present invention, a therapeutically effective amount or dose of aripiprazole may include 5 to 90 mg, preferably 5 to 60 mg, more preferably 5 to 30 mg, based on the free form and once-daily administration to humans.

In one embodiment of the present invention, the dose of the atypical antipsychotic agent including aripiprazole may be lower than the dose required for exhibiting a therapeutically effective amount when administered alone without the carbamate compounds of Formula 1. This is due to the combination with the carbamate compounds of Formula 1, which makes it possible to maintain an effective pharmacological effect while lowering the dose required for the pharmacological effect of the atypical antipsychotic agent.

According to one embodiment of the present invention, the combination weight ratio of the component a) a carbamate compound of Formula 1, or a pharmaceutically acceptable salt, solvate or hydrate thereof; to the component b) aripiprazole, or a pharmaceutically acceptable salt, solvate or hydrate thereof is 1:1 to 40:1, 1:1 to 20:1, 2:1 to 20:1, or 2:1 to 10:1.

The combination and pharmaceutical composition of the present invention can be prepared in various forms of oral or parenteral formulations, and may be administered by, for example, intravenous injection, intramuscular injection, intracutaneous injection, subcutaneous injection, intraduodenal injection, intraperitoneal injection or intrathecal injection, or they may also be administered by a transdermal route. In addition, the composition can be administered by any device capable of transferring the active substance to a target cell. The route of administration may vary depending upon the general condition and age of the subject to be treated, the nature of the treatment condition and the active ingredient selected.

A suitable dosage of the combination or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain a) the compounds of Formula 1 in the amount of 12.5 to 500 mg, 12.5 to 400 mg, 25 to 400 mg, 25 to 300 mg, 25 to 200 mg, 50 to 400 mg, 50 to 300 mg, 50 to 200 mg, or 100 to 200 mg, based on the free form; and b) aripiprazole in the amount of 5 to 90 mg, preferably 5 to 60 mg, more preferably 5 to 30 mg, based on the free form.

The pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

The pharmaceutical composition of the present invention further comprises one or more pharmaceutically acceptable carriers in addition to the active ingredients (a) and (b) as described above.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable antioxidants include, but are not limited to, tocopherol, ascorbic acid, gallate and the like.

In one embodiment, a suitable buffer may be citric acid monohydrate.

In one embodiment, suitable surfactants (emulsifiers) include, but are not limited to, anionic, cationic or nonionic surfactants, such as sodium laurate, sodium lauryl sulfate, sodium dodecanesulfonate, sodium oleyl sulfate, benzalkonium chloride, alkyltrimethyl ammonium bromide, glyceryl monooleate, polyoxyethylene dried sorbitan fatty acid ester, polyvinyl alcohol and dried sorbitan S or mixtures thereof.

In one embodiment, suitable binders include, but are not limited to, povidone, copovidone, methylcellulose, hydroxymethylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, colloidal silicon dioxide.

In one embodiment, suitable release-controlling agents (release-modifying excipients) include, but are not limited to, hydroxypropyl methylcellulose, polyethylene oxide, carbomer, pH-independent polymers such as alginic acid, pH-dependent polymers or mixtures thereof.

In one embodiment, suitable wetting agents include, but are not limited to, hypromellose (HPMC), a polyoxyethylene derivative of sorbitan esters, such as polysorbate 20 and polysorbate 80, lecithin, polyoxyethylene- and polyoxypropylene ether, sodium deoxycholate or mixtures thereof.

In one embodiment, suitable suspending agents include, but are not limited to, cellulose derivatives such as microcrystalline cellulose, methyl cellulose, sodium carboxymethyl cellulose, hydroxypropyl methyl cellulose, polyvinylpyrrolidone, alginate, chitosan, dextran, gelatin, polyethylene glycol, polyoxyethylene- and polyoxypropylene ether or mixtures thereof.

In one embodiment, suitable lubricants include, but are not limited to, long chain fatty acids and salts thereof, such as magnesium stearate and stearic acid, talc, glyceride wax or mixtures thereof.

The pharmaceutical composition of the present invention may be formulated into an injectable formulation such as an aqueous solution, a suspension or an emulsion, or may be formulated into pills, capsules, granules or tablets. In powders, the carrier may be a fine solid that can be mixed with the active ingredient in the form of a mixture, and in tablets, the active ingredient can be mixed with the carrier to have binding properties that can be tableted in an appropriate proportion and desired shape and size.

The pharmaceutical composition of the present invention may be prepared in capsule form.

For example, the pharmaceutical composition of the present invention may be prepared in capsules that contain a) the compounds of Formula 1 in the amount of 12.5 to 500 mg, 12.5 to 400 mg, 25 to 400 mg, 25 to 300 mg, 25 to 200 mg, 50 to 400 mg, 50 to 300 mg, 50 to 200 mg, or 100 to 200 mg, based on the free form; and b) aripiprazole in the amount of 5 to 90 mg of, preferably 5 to 60 mg, more preferably 5 to 30 mg, based on the free form; and gelatin and titanium dioxide as a capsule base. The above amount can be adjusted as needed.

The combinations and pharmaceutical compositions of the present invention have medicinal uses for the prevention, alleviation or treatment of schizophrenia.

According to one embodiment of the present invention, the symptoms of schizophrenia may be one or more selected from the group consisting of positive symptoms, negative symptoms, cognitive symptoms and residual symptoms of schizophrenia.

According to one embodiment of the present invention, the schizophrenia may be one or more selected from the group consisting of paranoid schizophrenia, disorganized schizophrenia, catatonic schizophrenia, undifferentiated schizophrenia, residual schizophrenia, post-schizophrenic depression, simple schizophrenia, unspecified schizophrenia, schizophreniform disorder, schizoaffective disorder, delusional disorder, brief psychotic disorder, shared psychotic disorder, psychotic disorder due to another medical condition, substance/medication-induced psychotic disorder, and psychotic disorder of unknown cause.

The antipsychotic activity of the carbamate compounds of Formula 1 and aripiprazole against schizophrenia can be tested through social interaction animal behavior tests used in drug development for the negative symptoms of schizophrenia (Neill J C, Grayson B, Kiss B, Gyertyán I, Ferguson P, Adham N, Effects of cariprazine, a novel antipsychotic, on cognitive deficit and negative symptoms in a rodent model of schizophrenia symptomatology, Eur Neuropsychopharmacol. 2016 January; 26(1):3-14). Since the effect of administration of N-methyl-D-aspartate (NMDA) receptor inhibitor and symptoms due to schizophrenia are similar, animals administered with N-methyl-D-aspartate (NMDA) receptor inhibitor can be used as the model of schizophrenia. Dizocilpine (MK-801) is an N-methyl-D-aspartate (NMDA) receptor inhibitor. In the dizocilpine-induced (MK-801-induced) social interaction animal behavior test, schizophrenia-like symptoms can be induced by administration of dizocilpine (Rung J P, Carlsson A, Ryden Markinhuhta K, Carlsson M L, (+)-MK-801 induced social withdrawal in rats; a model for negative symptoms of schizophrenia. Prog Neuropsychopharmacol Biol Psychiatry. 2005 June; 29(5): 827-32). Aripiprazole, known as an atypical antipsychotic drug, inhibits schizophrenia-like symptoms in proportion to the dose of dizocilpine (Deiana S, Watanabe A, Yamasaki Y, Amada N, Kikuchi T, Stott C, Riedel G, MK-801-induced deficits in social recognition in rats: reversal by aripiprazole, but not olanzapine, risperidone, or cannabidiol. Behav Pharmacol. 2015 December; 26 (8 Spec No): 748-65).

The dosage of the carbamate compounds of Formula 1 and aripiprazole for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "blend or mixture or combination" or "combined therapy" means that two or more drugs are used together, but does not necessarily mean a state in which two or more drugs are mixed. It means that two or more drugs may be present together in a single preparation in a mixed state, or may be used as separate preparations. In other words, the term "combination" includes a single preparation and also two separate preparations, so simultaneous, separate or sequential administration is possible.

As used herein, the term "composition" refers to a single preparation in which two or more drugs are present in a mixed state.

As used herein, the term "kit" typically means a finished product, and when two or more drugs are used, means a finished product containing these drugs in the form of a combination. Two or more drugs may be packaged in a single formulation in the finished product and administered simultaneously, or may be packaged in two separate formulations in the finished product and administered simultaneously, separately or sequentially.

Hereinafter, the present invention will be explained in more detail through working examples. The objects, features and advantages of the present invention will be readily understood through the following working examples. The present invention is not limited to the working examples described herein, but may be embodied in other forms. The working examples described herein are provided to ensure that the disclosed contents are thorough and complete, and that the technical concept of the present invention is sufficiently conveyed to a person skilled in the art to which the present invention pertains. Therefore, the present invention should not be limited by the following working examples.

Preparation Example: Synthesis of carbamic acid (R)-1-(2-chlorophenyl)-2-tetrazol-2-yl-ethyl ester Carbamic acid (R)-1-(2-chlorophenyl)-2-tetrazol-2-yl-ethyl ester (the compound of Formula 2, hereinafter referred to as "test compound") was prepared according to the method described in Preparation Example 50 of PCT Publication No. WO 2010/150946.

Example: Effects in Social Interaction Animal Behavior Tests in Animal Models with Schizophrenia-like Symptoms Induced by Dizocilpine Treatment Experimental Animals Male rats (Wistar, 4 weeks old, Orient Bio Co., Ltd.) were purchased, divided into 2 groups in an animal breeding room and acclimatized for more than 1 week on separate shelves. The experimental animals were housed and maintained in accordance with the Laboratory Animal Care Standards of the Institutional Animal Care and Use Committee (IACUC) under conditions of light-and-darkness cycle of 12 hours, a temperature of 22 to 25° C., a relative humidity of 40-60% and free access to food and water. After stabilization for more than a week, the rats were used in a social interaction animal behavior test in pairs of rats whose weight difference did not exceed 20 g.

Social Interaction Animal Behavior Tests

Symptoms resulting from administration of N-methyl-D-aspartate (NMDA) receptor inhibitor and symptoms due to schizophrenia are similar. Thus, an animal model is used in which schizophrenia-like symptoms can be induced by treatment of dizocilpine, an N-methyl-D-aspartate (NMDA) receptor inhibitor.

Dizocilpine (purchased from Sigma) was newly prepared by dissolving it in physiological saline used as a vehicle, and 4 hours before the experiment, a 0.1 mg/kg dose was administered subcutaneously in a volume of 1 ml per 1 kg of body weight of the rat.

Aripiprazole and the test compound were newly prepared by dissolving them in 30% polyethylene glycol 400 (Sigma) used as a vehicle. One hour before the experiment, a 0.003 mg/kg dose of aripiprazole and a 3 mg/kg dose of the test compound were administered orally in a volume of 1 ml per 1 kg of body weight of the rat.

The male rats were placed in the same observation box in pairs, allowing 1:1 interaction, and then the total time of sniffing, grooming, licking, mounting and crawling under or over the other rat which can be considered as active social interactions was measured for 5 minutes, and social interaction was evaluated based on that.

Statistical Analysis of Experimental Results

All data are expressed as mean±SEM. Statistical analysis of the total time of active social interactions between groups was performed using the GraphPad Prism ver. 5.04 program, and analyzed by one-way ANOVA (one-way analysis of variance) and Dunnett's multiple comparison test.

The total time average of active social interactions in the negative control group treated with dizocilpine only was observed to be 53.86±2.90 seconds, and the total time average of active social interactions in the positive control vehicle group was observed to be 69.63±3.13 seconds. The total time average of active social interactions was observed to be 57.52±3.04 seconds in the aripiprazole 0.003 mg/kg administration group, 56.78±2.19 seconds in the test compound 3 mg/kg administration group, and 63.76±1.87 seconds in the group administered with aripiprazole 0.003 mg/kg and the test compound 3 mg/kg.

TABLE 1

Effects of aripiprazole and the test compound on the social interaction animal behavior test treated with dizocilpine

| Drugs administered | Dizocilpine (mg/kg, sc [2]) | Aripiprazole (mg/kg, po [3]) | Test compound (mg/kg, po) | Number of animals | Social interaction[1] (Mean ± SEM) |
|---|---|---|---|---|---|
| Vehicle | — [4] | — | — | 20 pairs | 69.63 ± 3.13 |
| Dizocilpine | 0.1 | — | — | 20 pairs | 53.86 ± 2.90 |
| Aripiprazole | 0.1 | 0.003 | — | 20 pairs | 57.52 ± 3.04 |
| Test compound | 0.1 | — | 3 | 20 pairs | 56.78 ± 2.19 |
| Aripiprazole and test compound | 0.1 | 0.003 | 3 | 20 pairs | 63.76 ± 1.87 |

[1] Social interaction = Total time of active social interactions of sniffing, grooming, licking, mounting and crawling (unit: second)
[2] sc = mg/kg, subcutaneously
[3] po = mg/kg, per os
[4] — = Not treated Table 2 shows recovery rate (%) which represents the total time of active social interactions in the test compound and/or aripiprazole treated group and the positive control vehicle group, compared to that in the negative control group treated with dizocilpine only. The recovery rate was calculated as follows.

Recovery rate (%)=(Time of active social interactions in test group−Time of active social interactions in negative control group)/(Time of active social interactions in positive control group−Time of active social interactions in negative control group)×100

TABLE 2

Summary of recovery rate compared to negative control group in social interaction animal behavior test treated with dizocilpine and statistical significance

| Drugs administered | Number of animals | Recovery rate compared to negative control | Statistical significance compared to negative control ($P < 0.05$?) | Statistical significance compared to positive control ($P < 0.05$?) |
|---|---|---|---|---|
| Vehicle | 20 pairs | 100.0% | Significant | |
| Dizocilpine | 20 pairs | 0.0% | | Significant |

TABLE 2-continued

Summary of recovery rate compared to negative control
group in social interaction animal behavior test treated with
dizocilpine and statistical significance

| Drugs administered | Number of animals | Recovery rate compared to negative control | Statistical significance compared to negative control (P < 0.05?) | Statistical significance compared to positive control (P < 0.05?) |
|---|---|---|---|---|
| Aripiprazole | 20 pairs | 23.2% | Not significant | Significant |
| Test compound | 20 pairs | 18.5% | Not significant | Significant |
| Aripiprazole and test compound | 20 pairs | 62.8% | Significant | Not significant |

The aripiprazole administration group and the test compound administration group showed recovery rates of 23.2% and 18.5%, respectively, compared to the negative control group, and showed no statistically significant difference from the negative control group treated with dizocilpine only, and showed a statistically significant difference from the positive control group. While the respective administration of aripiprazole 0.003 mg/kg or the test compound 3 mg/kg did not show a significant recovery effect compared to the negative control group, the group administered with these doses together showed a recovery rate of 62.8% compared to the negative control group, showing a statistically significant difference from the negative control group and no statistically significant difference from the positive control group (FIG. 1).

From the above, it was confirmed that a combination of aripiprazole and the test compound shows a synergistic increase in the effect on social interaction. This indicates that these two drugs are effective in treating schizophrenia, especially the negative symptoms of schizophrenia.

What is claimed is:

1. A combination comprising (a) a carbamate compound of the following Formula 1, or a pharmaceutically acceptable salt, solvate or hydrate thereof; and (b) an antipsychotic agent selected from the group consisting of asenapine, clozapine, iloperidone, olanzapine, lurasidone, paliperidone, quetiapine, risperidone, ziprasidone, and a pharmaceutically acceptable salt, solvate or hydrate thereof:

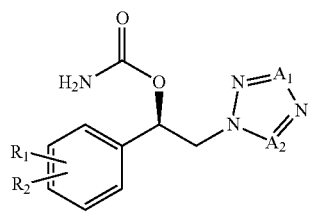

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

2. The combination according to claim 1, wherein $R_1$ and $R_2$ are each independently selected from the group consisting of hydrogen, halogen and $C_1$-$C_8$ alkyl.

3. The combination according to claim 1, wherein the carbamate compound of Formula 1 is carbamic acid (R)-1-(2-chlorophenyl)-2-tetrazol-2-yl-ethyl ester of the following Formula 2:

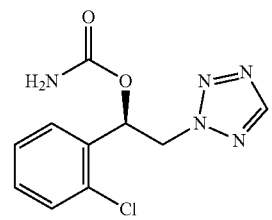

[Formula 2]

4. The combination according to claim 1, which comprises the compound of Formula 1 in an amount of 12.5 mg to 500 mg based on the free form.

5. The combination according to claim 1, which is in the form of a kit.

6. The combination according to claim 5, which contains (a) a first composition comprising a carbamate compound of Formula 1, or a pharmaceutically acceptable salt, solvate or hydrate thereof; and (b) a second composition comprising the antipsychotic agent, or a pharmaceutically acceptable salt, solvate or hydrate thereof, in a container.

7. A method for alleviating or treating schizophrenia, comprising:
administering to a subject in need thereof
a therapeutically effective amount of (a) a carbamate compound of the following Formula 1, or a pharmaceutically acceptable salt, solvate or hydrate thereof; and
a therapeutically effective amount of (b) an antipsychotic agent selected from the group consisting of asenapine, clozapine, iloperidone, olanzapine, lurasidone, paliperidone, quetiapine, risperidone, ziprasidone, and a pharmaceutically acceptable salt, solvate or hydrate thereof:

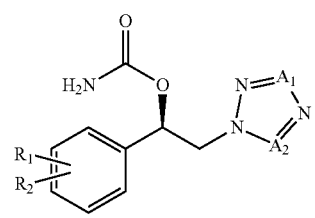

[Formula 1]

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

8. The method according to claim 7, wherein $R_1$ and $R_2$ are each independently selected from the group consisting of hydrogen, halogen and $C_1$-$C_8$ alkyl.

9. The method according to claim 7, wherein the carbamate compound of Formula 1 is carbamic acid (R)-1-(2-chlorophenyl)-2-tetrazol-2-yl-ethyl ester of the following Formula 2:

[Formula 2]

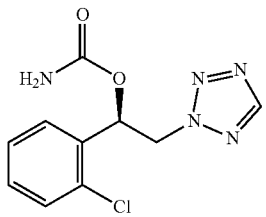

10. The method according to claim 7, wherein said schizophrenia exhibits one or more symptoms selected from the group consisting of positive symptoms, negative symptoms, cognitive symptoms and residual symptoms.

11. The method according to claim 7, wherein said schizophrenia is one or more selected from the group consisting of paranoid schizophrenia, disorganized schizophrenia, catatonic schizophrenia, undifferentiated schizophrenia, residual schizophrenia, post-schizophrenic depression, simple schizophrenia, unspecified schizophrenia, schizophreniform disorder, schizoaffective disorder, delusional disorder, brief psychotic disorder, shared psychotic disorder, psychotic disorder due to another medical condition, substance/medication-induced psychotic disorder, and psychotic disorder of unknown cause.

12. The method according to claim 7, which is prepared for mammalian administration.

13. The method according to claim 7, which comprises the compound of Formula 1 in an amount of 12.5 mg to 500 mg based on the free form.

14. The method according to claim 7, wherein the carbamate compound of Formula 1 and the antipsychotic agent are administered by intravenous injection, intramuscular injection, intracutaneous injection, subcutaneous injection, intraduodenal injection, intraperitoneal injection, or intrathecal injection.

15. A kit for the alleviation or treatment of schizophrenia, comprising:
(a) a carbamate compound of the following Formula 1, or a pharmaceutically acceptable salt, solvate or hydrate thereof; and
(b) aripiprazole, or a pharmaceutically acceptable salt, solvate or hydrate thereof:

[Formula 1]

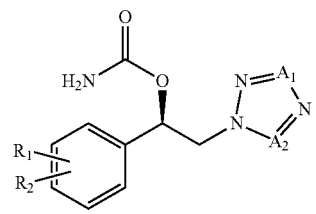

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

16. The method according to claim 7, wherein the carbamate compound of Formula 1 and the antipsychotic agent are administered simultaneously or sequentially.

17. The method according to claim 7, wherein the carbamate compound of Formula 1 and the antipsychotic agent are administered separately.

* * * * *